(12) United States Patent
Hoffman et al.

(10) Patent No.: US 11,971,905 B2
(45) Date of Patent: Apr. 30, 2024

(54) SYSTEMS AND METHODS FOR SYNCHRONIZING NODES OF A ROBOTIC SYSTEM

(71) Applicant: INTUITIVE SURGICAL OPERATIONS, INC., Sunnyvale, CA (US)

(72) Inventors: Brian D. Hoffman, Mountain View, CA (US); Joshua Radel, Menlo Park, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 18/309,711

(22) Filed: Apr. 28, 2023

(65) Prior Publication Data
US 2023/0289366 A1 Sep. 14, 2023

Related U.S. Application Data

(63) Continuation of application No. 16/795,162, filed on Feb. 19, 2020, now Pat. No. 11,687,556, which is a
(Continued)

(51) Int. Cl.
*G06F 16/00* (2019.01)
*A61B 34/00* (2016.01)
(Continued)

(52) U.S. Cl.
CPC .......... *G06F 16/27* (2019.01); *A61B 34/00* (2016.02); *A61B 34/37* (2016.02); *G06F 9/542* (2013.01);
(Continued)

(58) Field of Classification Search
None
See application file for complete search history.

(56) References Cited

U.S. PATENT DOCUMENTS 4,860,285 A * 8/1989 Miller ............... H04Q 11/0471
370/507
6,263,347 B1 7/2001 Kobayashi et al.
(Continued)

FOREIGN PATENT DOCUMENTS

CN 102571485 A 7/2012
CN 102830645 A 12/2012
(Continued)

OTHER PUBLICATIONS

Eugster P.T., et al., "The Many Faces of Publish/Subscribe," ACM Computing Surveys, Jun. 2003, vol. 35(2), pp. 114-131, XP002424894.
(Continued)

*Primary Examiner* — Anhtai V Tran
(74) *Attorney, Agent, or Firm* — Haynes & Boone, LLP.

(57) ABSTRACT

A synchronization system node may comprise one or more processors and a synchronization database. The synchronization database may comprise a subscriber list of a plurality of subscribers, a first buffer including a plurality of attributes in a first state, and a second buffer including the plurality of attributes in a second state. The node may be configured to receive updates for one or more of the plurality of attributes and store, to the first buffer, the updates for the one or more of the plurality of attributes to update the plurality of attributes of the first buffer to an updated first state. While receiving the updates from the publisher, the nod may publish, from the second buffer to a first subscriber of the plurality of subscribers, one or more of the plurality of attributes in the second state.

20 Claims, 9 Drawing Sheets

Related U.S. Application Data continuation of application No. 15/814,214, filed on Nov. 15, 2017, now Pat. No. 10,592,529, which is a continuation of application No. 15/242,408, filed on Aug. 19, 2016, now Pat. No. 9,830,371, which is a continuation of application No. 14/181,499, filed on Feb. 14, 2014, now Pat. No. 9,424,303.

(60) Provisional application No. 61/765,559, filed on Feb. 15, 2013.

(51) Int. Cl.
*A61B 34/37* (2016.01)
*G06F 9/54* (2006.01)
*G06F 16/23* (2019.01)
*G06F 16/27* (2019.01)

(52) U.S. Cl.
CPC ...... *G06F 16/2365* (2019.01); *G06F 16/2379* (2019.01); *G06F 16/273* (2019.01)

(56) References Cited

U.S. PATENT DOCUMENTS

| | | |
|---|---|---|
| 6,421,570 B1 | 7/2002 | McLaughlin et al. |
| 6,711,578 B1 | 3/2004 | McCaw et al. |
| 7,113,963 B1 | 9/2006 | McCaw |
| 7,529,599 B1 | 5/2009 | Bhatt et al. |
| 8,635,373 B1 | 1/2014 | Supramaniam et al. |
| 9,424,303 B2 | 8/2016 | Hoffman et al. |
| 9,830,371 B2 | 11/2017 | Hoffman et al. |
| 10,592,529 B2 | 3/2020 | Hoffman et al. |
| 2002/0099787 A1* | 7/2002 | Bonner ............... H04L 69/329 709/216 |
| 2005/0055132 A1 | 3/2005 | Matsumoto et al. |
| 2005/0278346 A1 | 12/2005 | Shang et al. |
| 2006/0209868 A1 | 9/2006 | Callaghan |
| 2007/0198629 A1 | 8/2007 | Ganguly et al. |
| 2009/0164202 A1 | 6/2009 | Loennemark et al. |
| 2010/0174680 A1 | 7/2010 | Yamagishi et al. |
| 2011/0060957 A1 | 3/2011 | Bogucharov et al. |
| 2011/0231014 A1 | 9/2011 | Krajewski et al. |
| 2012/0254108 A1 | 10/2012 | Wedewer et al. |
| 2014/0019581 A1 | 1/2014 | Baillargeon et al. |
| 2020/0192911 A1 | 6/2020 | Hoffman et al. |

FOREIGN PATENT DOCUMENTS

| | | |
|---|---|---|
| JP | 2000235547 A | 8/2000 |
| JP | 2001514407 A | 9/2001 |
| JP | 2007234014 A | 9/2007 |
| JP | 2010021805 A | 1/2010 |
| JP | 2010021806 A | 1/2010 |
| JP | 2010105150 A | 5/2010 |
| KR | 20110000689 A | 1/2011 |
| WO | WO-9910788 A1 | 3/1999 |
| WO | WO-9950726 A1 | 10/1999 |

OTHER PUBLICATIONS

Extended European Search Report for Application No. 14751546.4, dated Sep. 23, 2016, 12 pages.
Extended European Search Report for Application No. EP20152283. 6, dated May 13, 2020, 10 pages.
International Search Report and Written Opinion for Application No. PCT/US2014/016615, dated May 30, 2014, 10 pages.
Kang J.S., et al., "Remote Variable Access Protocol for Data-Centric Telerobotics", Automation and Systems (ICCAS), 12th International Conference on Control, IEEE, Oct. 17, 2012, pp. 1985-1989, XP032291535.
Muhl G., "Generic Constraints for Content-Based Publish/Subscribe," Security in Communication Networks, Third International Conference, Revised Papers/SCN, Sep. 11-13, 2002, pp. 211-225, XP002500569, [retrieved on Sep. 5, 2001], Retrieved from the Internet [URL: http://www.kbs.cs.tu-berlin.de/publications/fulltext.coopis2001.pdf ].
Pardo-Castellote G., "OMG Data-Distribution Service: Architectural Overview," Proceedings of the 23rd International conference on Distributed Computing Systems Workshops (ICDCSW'03), 2003, pp. 200-206, XP010642373.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Ying L., et al., "Survey of Publish Subscribe Event Systems," Technical Report 574, Jul. 2002, pp. 1-19, XP007919204, [online], [retrieved on Sep. 12, 2016], Retrieved from the Internet: URL: http://www.cs.indiana.edu/pub/techreports/TR574.pdf.

\* cited by examiner

SYSTEMS AND METHODS FOR SYNCHRONIZING NODES OF A ROBOTIC SYSTEM

RELATED APPLICATIONS

This application is a continuation of U.S. patent application Ser. No. 16/795,162, filed Feb. 19, 2020, which is a continuation of U.S. patent application Ser. No. 15/814,214, filed Nov. 15, 2017, which is a continuation of U.S. patent application Ser. No. 15/242,408, filed Aug. 19, 2016, now issued U.S. Pat. No. 9,830,371, which is a continuation of U.S. patent application Ser. No. 14/181,499, filed Feb. 14, 2014, now issued U.S. Pat. No. 9,424,303, which claims priority to U.S. Provisional Application No. 61/765,559, filed on Feb. 15, 2013, each of which are incorporated herein by reference in their entireties.

BACKGROUND

Technical Field

The present disclosure is related to systems and methods for synchronizing nodes of a robotic system. In particular, the present disclosure is related to synchronization databases that can be executed at each node of the robotic system, the synchronization databases allowing for the subscription and publishing of updated attributes between the nodes of the robotic system.

Discussion of Related Art

Certain applications have high bandwidth requirements and strict synchronization, latency, and reliability requirements for communications. Robot-assisted surgery, for example, requires low-latency to transmit control and feedback signals in real time. The synchronization and latency requirements of such applications are strict, because ideally there should be as little lag as possible between the movements of a surgeon controlling a master input and the movements of the robot slaved to the master.

Complex systems, including robot-assisted surgery systems, include many components, referred to generally herein as "nodes", that work together within the system and therefore need to be able to remain synchronized. For each of these coupled nodes, the synchronization is often performed by a first node sending data requests to a second node, to which the second node will respond to the request by providing the requested data to the first node. In some instances, a first node will check for the presence of the second node and a third node, and if the second and third node are found to be present, the first node will then push data to the second and third nodes. If the second or third nodes are disconnected from the first node and then reconnected, the first node may not be notified that the second or third node was disconnected, and as a result the reconnected node may be missing data that the first node sent during the disconnection. Furthermore, when a new node is coupled to the first node, the first node may not check for the presence of the new node and, thus, not provide any data to the new node so that data at the new node is not synchronized with the first node's data. Ultimately, the need for the system to continually check for the presence of nodes and then send data to each of the nodes to remain synchronized may create unnecessary system traffic that can slow down the system or overflow message queues.

What is needed are systems and methods that permit the automatic synchronization of nodes in a system with minimal system traffic and that allow for the rapid synchronization of new nodes to the system.

SUMMARY

Consistent with some embodiments, a robotic system is provided. The robotic system includes a publishing node including at least one first synchronization database that includes a plurality of attributes, each of the attributes including a tag identifying the attribute and data, a flag associated with each of the attributes, and a subscriber list. The system also includes a subscriber node including at least one second synchronization database. The publishing node is configured to set the flag associated with the attributes when the attributes are written in the at least one first synchronization database or when the data included in the attributes are modified and publish the flagged attributes to the subscriber node.

Consistent with some embodiments, there is also provided a method for synchronizing data across nodes of a robotic system. The method includes transmitting, from a publishing node, an advertising message advertising attributes stored in a server instance of a synchronization database executing on the publishing node, receiving, by a subscribing node coupled to the publishing node, the advertising message and transmitting, by the subscribing node, a subscription message indicating the attributes stored in the server instance of a synchronization database executing on the publishing node that the at least one subscribing node wants to subscribe to. The method also includes adding, by the publishing node, the subscribing node to a subscription list maintained in the server instance of a synchronization database executing on the publishing node, setting, by the publishing node, a flag for each of the subscribed attributes, transmitting, by the publishing node, a synchronization packet including each of the flagged attributes to the subscribing node, and clearing the flag for each of the transmitted attributes.

Further consistent with some embodiments, there is also provided a non-transitory computer-readable medium having instructions for execution by one or more processors of a robotic system, when executed, cause the one or more processors to perform a method for synchronizing nodes of the robotic system. The method includes transmitting, from a publishing node, an advertising message advertising attributes stored in a server instance of a synchronization database executing on the publishing node, receiving, by a subscribing node coupled to the publishing node, the advertising message, and transmitting a subscription message from the subscribing node to the publishing node, the subscription message indicating the attributes stored in the server instance of a synchronization database executing on the publishing node that the at least one subscribing node wants to subscribe to. The method also includes adding the subscribing node to a subscription list maintained in the server instance of a synchronization database executing on the publishing node, setting a flag for each of the subscribed attributes in the server instance of a synchronization database executing on the publishing node, transmitting a synchronization packet from the publishing node to the subscribing node, the synchronization packet including each of the flagged attributes, and clearing the flag for each of the transmitted attributes in the server instance of a synchronization database executing on the publishing node.

These and other embodiments will be described in further detail below with respect to the following figures.

Figure 1:
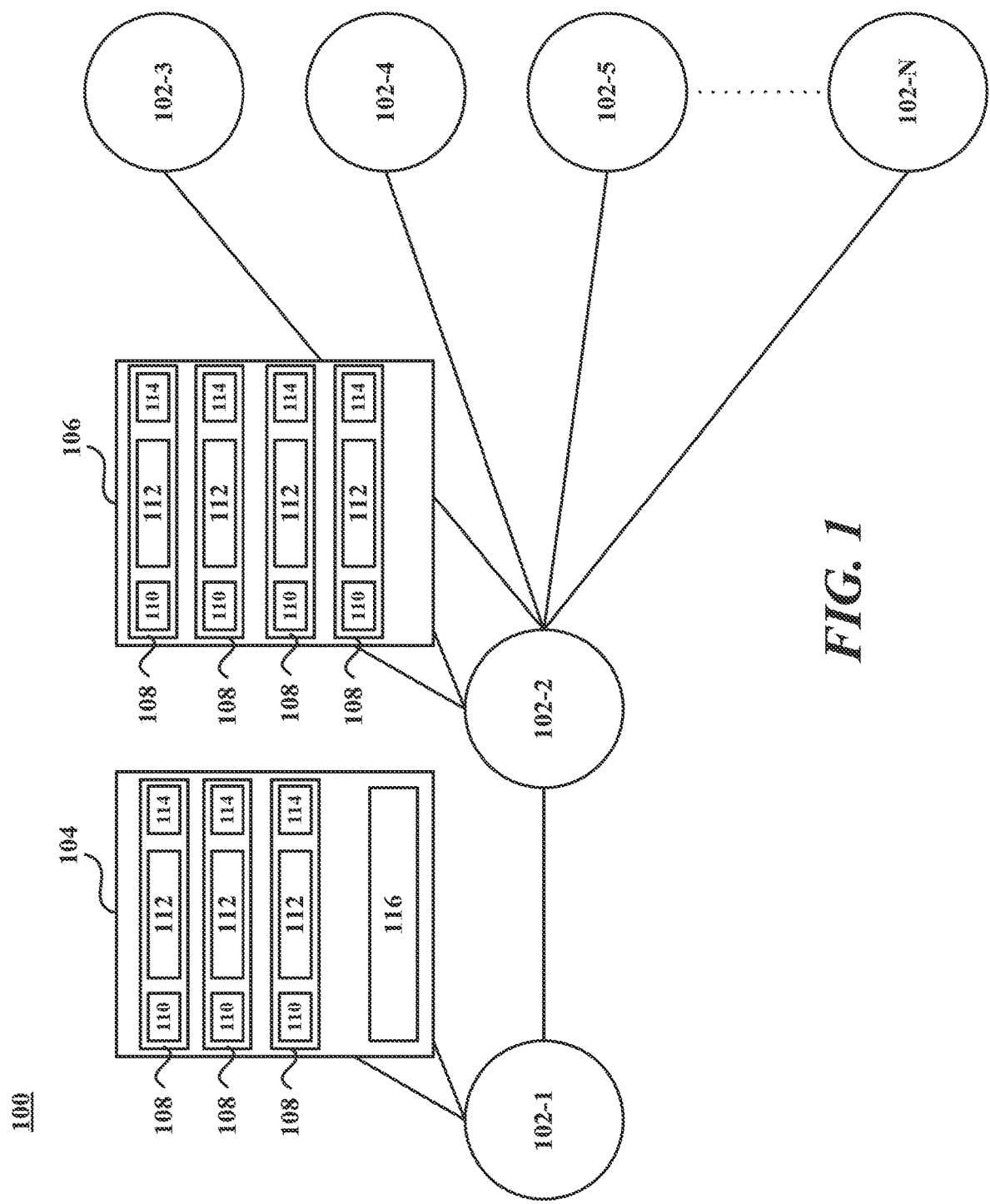
FIG. 1 is a diagram illustrating a system for synchronizing nodes in a system using instances of a synchronization database, consistent with some embodiments.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Various mechanical, compositional, structural, electrical, and operational changes may be made without departing from the spirit and scope of this description and the claims. In some instances, well-known circuits, structures, and techniques have not been shown in detail in order not to obscure the invention. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

FIG. 1 is a diagram illustrating a system 100 for synchronizing nodes in a system using instances of a synchronization database, consistent with some embodiments. As shown in FIG. 1, system 100 includes a plurality of interconnected nodes 102-1 to 102-N (referred to collectively as "nodes 102"). Consistent with some embodiments, each node 102 may be a device, a component of a robotic system, one or more processors, individual tasks that are being performed by the one or more processors. Nodes 102 may include any appropriate combination of hardware and/or software having one or more processors and capable of reading instructions stored on a non-transitory machine-readable medium for execution by the one or more processors. Such instructions may include instructions for creating one or more instances of a synchronization database, as described herein.

Returning to FIG. 1, nodes 102 include a first node 102-1 coupled to a second node 102-2 which, in turn, is coupled to a plurality of nodes 102-3 to 102-N. Although not shown in FIG. 1, node 102-1 may be directly coupled to additional nodes in a way similar to the connection with node 102-2. Consistent with some embodiments, a memory (not shown) is associated with each node 102. Further, one or more processors can also be associated with each node 102. Instructions for creating an instance of a synchronization database may be stored in the memory, and the one or more processors can execute these instructions to create one or more instances of a synchronization database at each node 102. Consistent with some embodiments, the synchronization database is a software container object that (i) stores data attributes, such as states or events, (ii) supports the aggregation of data changes on one node, referred to as a publishing node, and (iii) supports the publication of that changed data to one or more subscriber nodes. The synchronization database may accomplish this through the execution of one or more synchronization applications that are executed at each node to perform the functions necessary to subscribe to a publishing node and receive data changes or publish data changes to one or more subscribing nodes. The synchronization applications may be referred to as a publishing application for a publishing node and a subscribing application for a subscribing node.

As shown in FIG. 1, node 102-1 is executing a server instance of a synchronization database 104, and acts as a publishing node and node 102-2 is executing a client instance of a synchronization database 106, and acts as a subscribing node. A synchronization database, both server instances and client instances, may store a set of data-vectors, referred to as attributes 108, a list of subscribing nodes 116, and an additional state (not shown) that may be used to manage synchronization. Attributes 108 may refer to data that includes states or events in system 100, and may further include counters and time stamps. Attributes 108 may also refer to data that are behavioral elements used to describe behaviors of system 100. Consistent with some embodiments, attributes 108 may refer to user interface (UI) states or events that may be visual representations of states or events occurring on one node which can be published to additional nodes to update the additional nodes of the events and/or replicate the visual representation of these states or events at the additional nodes. Attributes 108 may also be stored in one or more databases, such as a database 104 associated with node 102-1 and database 106 associated with node 102-2 shown in FIG. 1.

As shown in FIG. 1, attributes 108 include a tag 110, data 112, and an associated flag 114 that can be set or cleared. Although database 104 associated with node 102-1 and database 106 associated with node 102-2 are shown as having only three or four attributes, the number of attributes is only limited by the memory allocated for the synchronization database instance on each node 102. Consistent with some embodiments, attributes 108 stored in database 104 or database 106 are sent to a requesting node when the node associated with database 104 or database 106 receives a query from the requesting node.

Each attribute 108 stored in a synchronization database is uniquely identified by a tag 110. Consistent with some embodiments, tag 110 may be a 32-bit tag and may support efficient database operation by using a hash-table lookup function. Flag 114 indicates whether attribute 108 requires publishing to synchronize attribute 108 with subscribing client database 106. When attribute 108 is written to database 104 or otherwise modified in database 104 such that the corresponding attribute 108 stored by database 106 may be different, flag 114 is set. Node 102-1 may modify one or more attributes 108, setting flag 114 for each modified attribute 108. Node 102-1 may then call a "publish" method on its associated database 104, to publish all attributes 108 stored in database 104 with flag 114 set to subscribing nodes 102, such as node 102-2. After an attribute 108 is published, flag 114 is cleared in database 104. Flag 114 may be a field that includes a bit for each subscribing node 102.

As shown in FIG. 1, database 104 also includes a subscriber list 116, which is a listing of nodes 102 and their associated databases that have subscribed to one or more attributes 108 stored in database 104. Consistent with some embodiments, database 104 advertises its stored attributes 108. In such embodiments, database 104 may periodically transmit a signal to all coupled nodes 102 indicating the attributes 108 and data that it is storing so that other nodes, such as node 102-2, can determine if it should fully or partially subscribe to one or more of the attributes 108 stored in database 104. For example, database 104 may transmit an advertise message upon an initial connection with subscribing node 102 or when database 104 starts up. At the same time, database 106 periodically transmits a discover message to attempt to identify a node having an associated database that stores data that database 106 requires. For example, database 106 may transmit a discover message upon an initial connection with publishing node 102-1 having database 104 or when database 106 starts up. When database 104 receives a discover message or database 106 receives an advertise signal, database 104 and database 106 will establish a link. Upon receiving a discover message, database 104 will transmit a discover reply signal to database 106. Upon receiving an advertise signal or a discover reply signal, database 106 will send a subscribe message to database 104, establishing the link of the two nodes and the subscription of database 106 associated with node 102-2 to one or more attributes 108 stored in database 104 associated with node 102-1. Node 102-2 is then added to subscriber list 116.

Node 102-2 and it associated database 106 may subscribe to all attributes 108 stored in database 104 or may only subscribe to certain attributes. Each node 102 may have a unique identifier stored in subscriber list 116 for uniquely identifying the subscribed node. When a node 102 subscribes to attributes 108 stored in database 104, the node is allocated a flag 114 for each subscribed attribute 108 such that when the subscribed attribute is modified, flag 114 will be set. When a node 102 initially subscribes to a server database 104, all attributes 108 to which it is subscribed will have flag 114 set. The subscribing node, such as node 102-2 and its associated database 106, may then send a reply message to database 104 indicating that it is ready to receive all attributes 108 having flag 114 set. While database 104 waits for the reply message from the subscribing node, such as node 102-2 and its associated database 106, database 104 will aggregate any further changes or modifications to subscribed attributes 108 and set flag 114 accordingly. After receiving the reply message, database 104 will then publish the attributes having flag 114 set and then clear flag 114. After the attributes 108 are received they are checked for errors, and if there are no errors, the database of the subscribing node transmits an acknowledgment message to database 104. Any subscribed attributes 108 that are modified while database 104 waits for the acknowledgment message will be published to the database of the subscribing node after receiving the acknowledgement message. If the database of the receiving node determines that the received attributes 108 include errors, the database will enter an error state and request that database 104 retransmit the subscribed attributes. The method of publishing attributes 108 is discussed further with respect to FIG. 4, below.

Just as node 102-2 executes a client instance of a synchronization database to subscribe to attributes 108 stored in database 104 at node 102-1, nodes 102-3 to 102-N may also execute a client instance of a synchronization database to subscribe to attributes in the synchronization database at node 102-2.

Consistent with some embodiments, a synchronization database instance may be double-buffered so that it may act as both a client and a server to republish received attributes to downstream nodes. For example, node 102-2 may execute a client instance of a synchronization database to subscribe to attributes stored in database 104 of node 102-1. Attributes (with an updated state) received from database 104, possibly spanning multiple synchronization packets (described below with reference to FIG. 2), are stored in a first inactive/ "background" buffer at node 102-2. At the same time, the same attributes (with a current state) stored in a second active/"foreground" buffer at node 102-2 can be published to subscribing nodes 102-3 to 102-N. When the synchronization update between nodes 102-1 and 102-2 is complete, the background and foreground buffers are swapped so that the new foreground buffer has the most recent attributes received from node 102-1. Then, the attributes 108 held at node 102-2 in the updated foreground buffer, are used to update downstream nodes 102-3 to 102-N. Node 102-2 republishes the attributes 108, received from node 102-1 into the background buffer and then swapped into the foreground buffer, to any nodes 102-3 to 102-N that have subscribed to receive the attributes from node 102-2. In the example described, it is not necessary for node 102-2 to execute a server instance to publish attributes 108 received from node 102-1 to nodes 102-3 to 102-N, as the client instance is capable of republishing attributes 108 as described. However, node 102-2 is capable of executing both a server instance and a client instance of a synchronization database, as described below with respect to FIG. 3.

Moreover, although node 102-2 is described as being double-buffered to republish received attributes to downstream nodes, any node 102 that subscribes to another node may benefit from being double-buffered, even if the node is not republishing the received attributes to downstream nodes. For example, a subscribing node, such as node 102-3 may receive modified attributes from a publishing node, such as 102-2, in synchronization packets that will be described further with respect to FIG. 2, below. These synchronization packets will be received by node 102-3 and be stored in the background buffer as they are received. Once node 102-3 has received the synchronization packets for a particular synchronization operation, the background buffer will be swapped with the foreground buffer, giving node 102-3 an atomic view of the aggregated transaction, and allowing node 102-3 to receive further synchronization packets to be stored in the just-swapped foreground buffer, which now acts as the background buffer.

Consistent with some embodiments, publishing nodes such as 102-1 having database 104, may transmit a heartbeat signal to those nodes 102 that subscribe to its attributes 108, such as node 102-2 having database 106. The heartbeat signal may be a synchronization update signal having synchronization packets with no attributes. Consistent with some embodiments, the heartbeat signal may be transmitted periodically from publishing node 102-1 after an attribute synchronization, and the periodic transmission is reset after each attribute synchronization. When receiving the heartbeat signal, database 106 will view the heartbeat signal as a synchronization signal and send a reply message just as if the signal included updated attributes. Subscribing nodes, such as node 102-2, having client database 106 will periodically receive this heartbeat signal and therefore be aware that database 104 is online and database 106 will receive updated attributes to which it has subscribed. If a subscribing node stops receiving the periodic heartbeat signal, it will be aware that database 104 of node 102-1 is offline and not providing updated attributes. Database 106 may then begin to analyze advertising messages transmitted from publishing nodes, may begin to issue discover messages to server nodes, and may subscribe to the publishing nodes having desired attributes. In some embodiments, for example after a communication break between publishing and subscribing nodes, database 106 of node 102-2 may re-subscribe to database 104 of node 102-1 to receive desired attributes.

If a database of any subscribing node 102, goes offline for a predetermined period of time sufficient for a publishing node to consider the subscribing node and/or its associated database as being "dead" due to the lack of received reply messages, the database of the publishing node may remove the subscribing node and its associated database from its subscriber list. Once the subscribing node, comes back online, it may re-subscribe to one or more attributes stored in the database of the publishing node in the same way it did previously. That is, the re-subscribing node 102, will receive the advertisement message transmitted from the publishing node indicating the attributes 108 and data available from its associated database, or send a discover message indicating attributes that it wants to subscribe to, and it will then subscribe messages to one or more attributes 108 stored in the database of the publishing node. The database of the publishing node will then add the re-subscribing node back to its subscriber list 116, and will set the flag 114 for each of the indicated attributes 108. Upon receipt of an initial "sync-reply" issued from the database of the re-subscribing node the database of the publishing node will publish the attributes with flag 114 set. The database of the re-subscribed node 102 will then receive any future modifications to its subscribed attributes 108.

Figure 2:
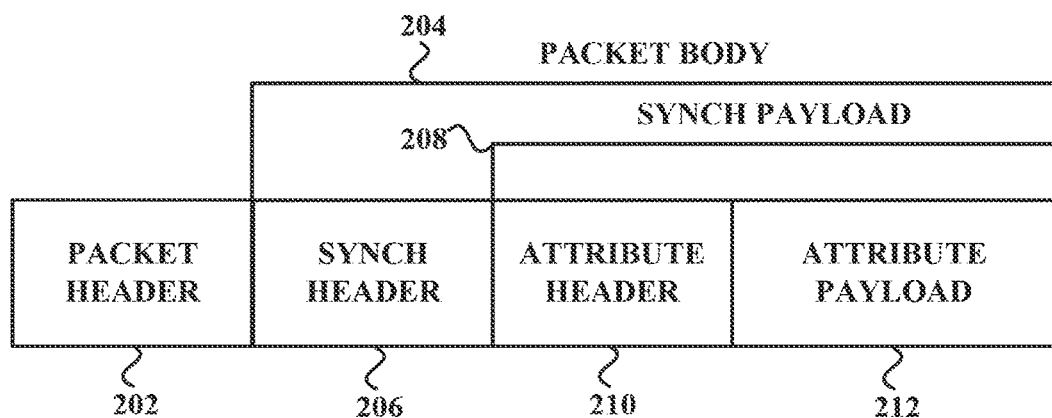
FIG. 2 is a diagram illustrating a synchronization packet, consistent with some embodiments.

FIG. 2 is a diagram illustrating a synchronization packet, consistent with some embodiments. When a database of a publishing node publishes attributes 108 to subscribing nodes 102, the attributes 108 are transmitted as synchronization packets 200. Synchronization packet 200 includes a packet header 202 and a packet body 204. Packet body 204 includes a synchronization header 206 and attributes 108 to be synchronized in the synchronization payload 208. Each of the attributes 108 to be synchronized may include an attribute header 210 and an attribute payload 212. Consistent with some embodiments, synchronization header 206 may include a synchronization state (such as reset, start, continue, and end), a serial number associated with a group of attributes being published in the same publish event, and a packet count. Attribute header 210 may include attribute tag 110, a timestamp of the last modification of attribute, and the length of the attribute payload 212 following attribute header 210. Consistent with some embodiments, attribute header 210 may also include an offset allowing the attribute payload to be split and transferred across multiple synchronization packets 200.

Consistent with some embodiments, a database of a publishing node, such as database 104 shown in FIG. 1, will identify attributes 108 having flag 114 set and prepare these attributes for publishing to databases of subscribing nodes, such as database 106 of node 102-2. The database of the publishing node can then arrange the attributes 108 into synchronization packets 200, in which a first packet will be indicated as "start" in synchronization header 206, subsequent packets will be indicated as "continue" in synchronization header 206, and the final packet will be indicated as "end" in synchronization header 206. Consistent with some embodiments, if only two synchronization packets are arranged, they will respectively be indicated as "start" and "end" in synchronization header 206. If only one synchronization packet 200 is arranged, it will be indicated as "end" in synchronization header 206. Once the synchronization packets 200 are structured, they are then transmitted by the database of the publishing node and received by the database of the subscribing node. As each synchronization packet 200 is received by the database of the subscribing node, attributes 108 will be unpacked and written into the database. Once the database of the subscribing node processes a synchronization header 206 having an "end" designation, an acknowledgement message to the publishing node. Then, consistent with some embodiments, the subscribing node will act as a publishing node and publish attributes to its subscribed nodes 102.

Figure 3:
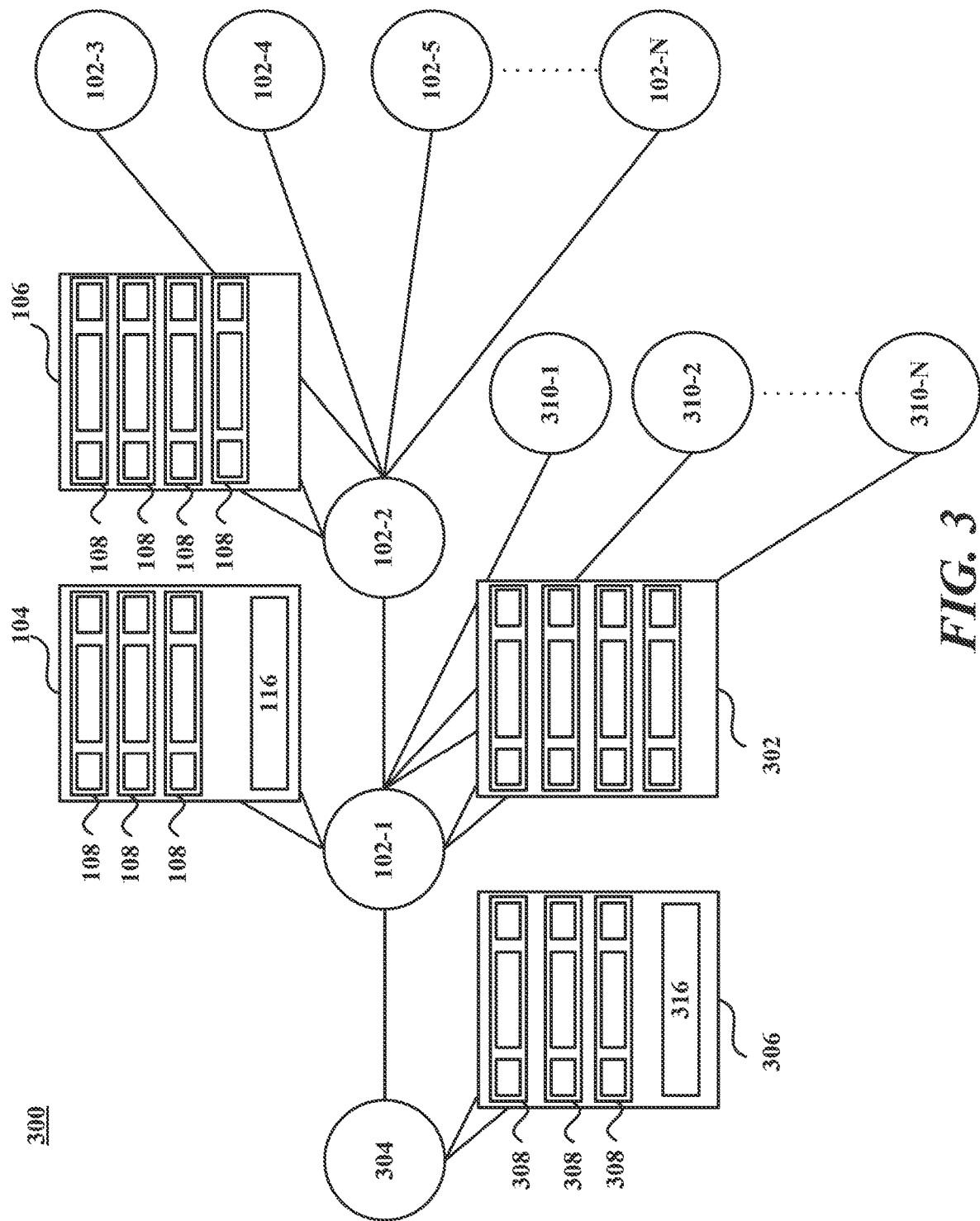
FIG. 3 is a diagram illustrating a system in which multiple synchronization database instances are executing on nodes, consistent with some embodiments.

FIG. 3 is a diagram illustrating a system in which multiple synchronization database instances are executing on nodes 102, consistent with some embodiments. As shown in FIG. 3, each node 102 is capable of executing multiple synchronization database instances. For example, as shown in FIG. 3, node 102-1 is executing both (i) a server instance of a synchronization database 104 for publishing attributes to subscribing node 102-2 and associated database 106, and (ii) a client instance of a synchronization database instance 302 that subscribes to node 304 and its associated database 306. Consequently, database 302 is subscribed to attributes 308 in database 306, as noted in subscriber list 316, and database 302 will receive these attributes 308 when they are written or otherwise modified in database 306. At the same time, database 104 will publish written or otherwise modified attributes 108 to database 106 of subscribed node 102-2 and to additional coupled nodes 310-1 to 310-N, if so subscribed. Each node 102, 304, and 310 is capable of running multiple instances of a synchronization database such that it can be both a subscribing node and a publishing node. And, consistent with some embodiments, one or more of the databases executing at a single node may be double buffered, as described above.

Thus a single node may be both a publishing and subscribing node, and these publishing and subscribing functions may be carried out with either a single attribute data synchronization database or with multiple attribute data synchronization databases. A single node may publish a first set of attributes to a corresponding first set of one or more subscribing nodes and a second set of attributes to a corresponding second set of one or more subscribing nodes. Similarly, a single node may subscribe to a first set of attributes from a first publishing node and a second set of attributes from a second publishing node. And, the various features discussed above, such as heartbeat signals, may be features of one or more of the various synchronization databases. In addition, it can be seen that consistent with some embodiments a set of interconnected nodes may perform attribute updates not just in a single "downstream" direction but in both directions.

Figure 4A:
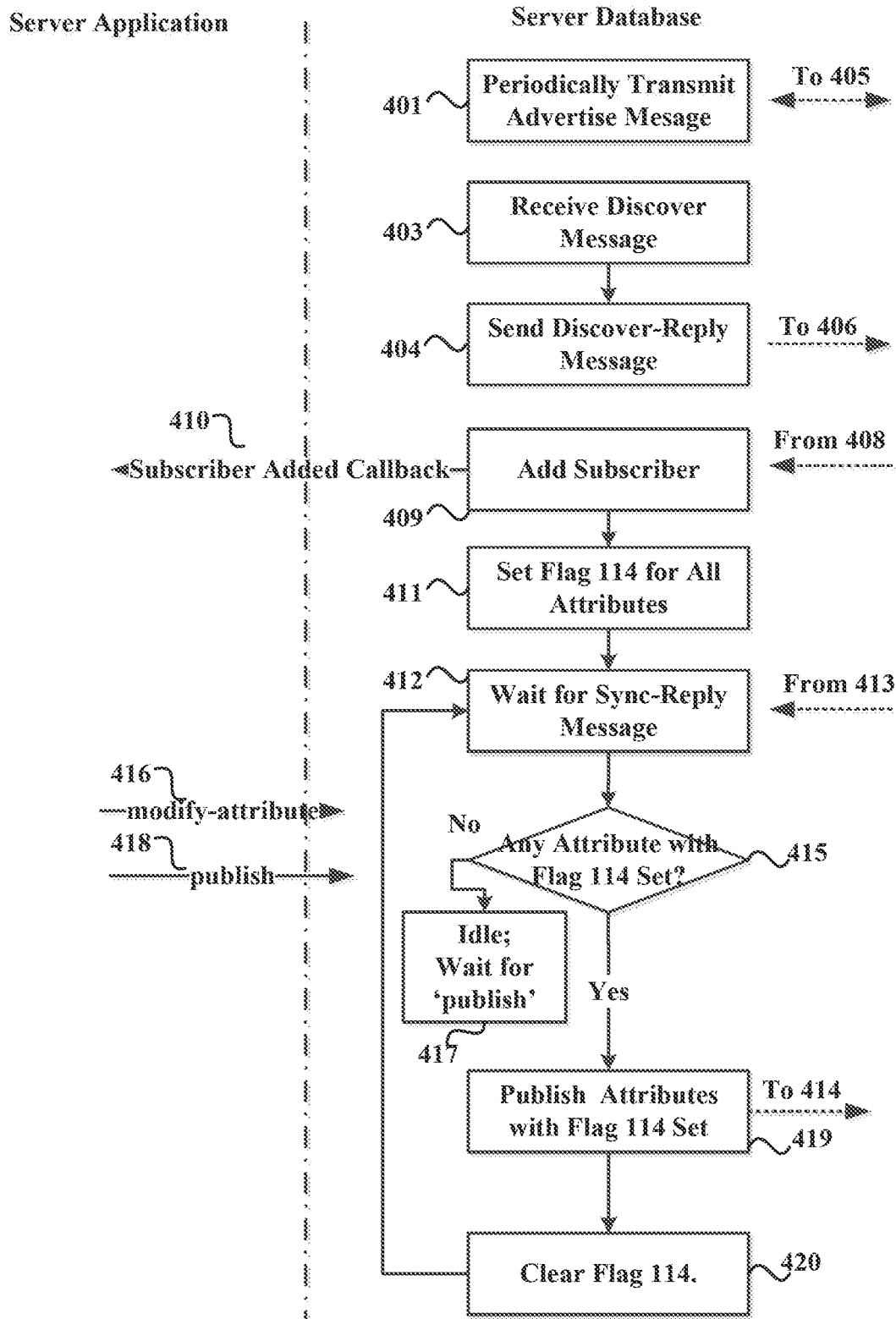
FIGS. 4A and 4B are flowcharts illustrating a method of synchronizing attributes between a server database and a client database, consistent with some embodiments.
Figure 4B:
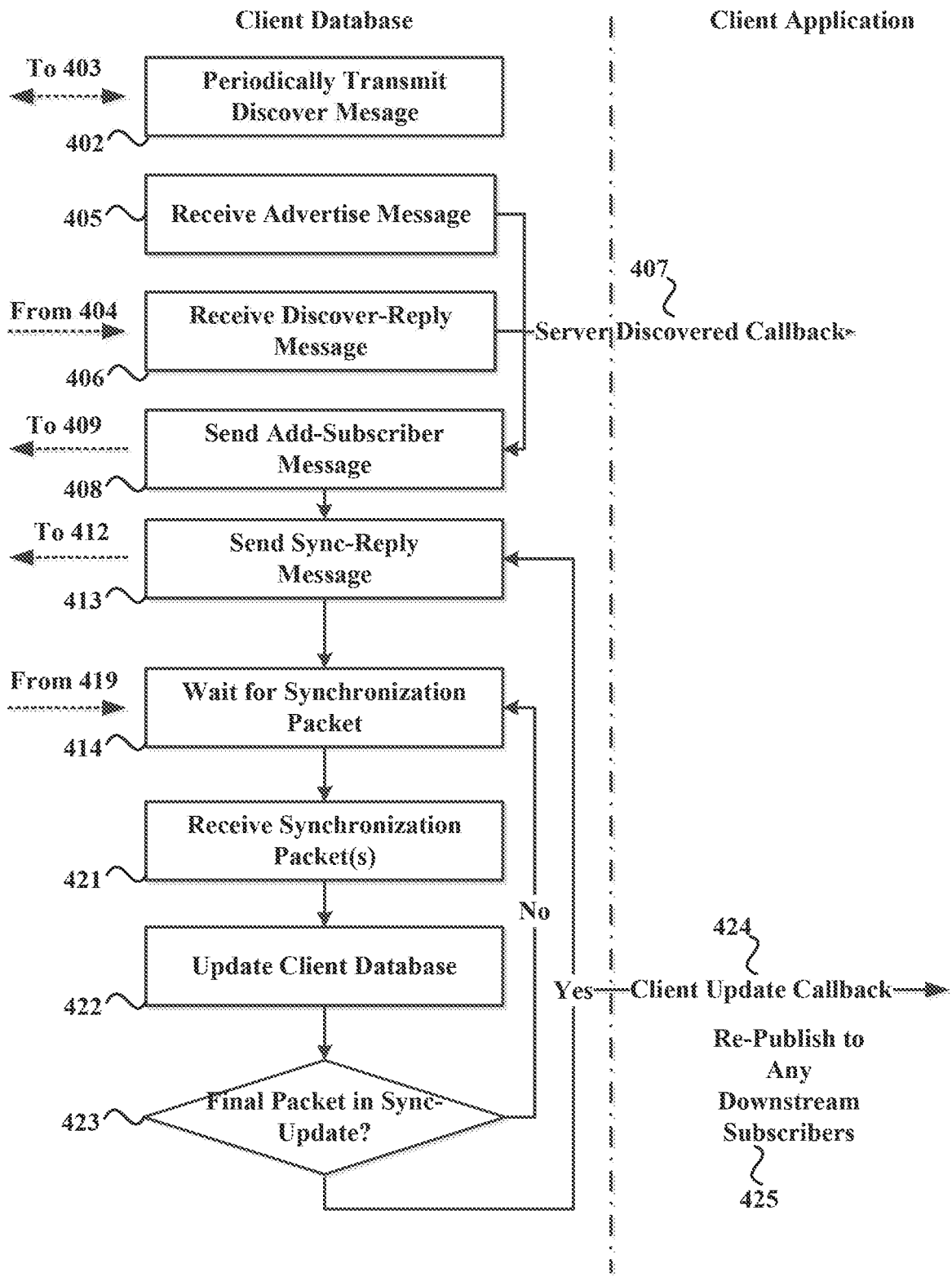

FIGS. 4A and 4B are flowcharts illustrating a method of synchronizing attributes between a publishing node and a subscribing node, consistent with some embodiments. In particular, FIG. 4A illustrates the actions performed by database 104 of node 102-1, and FIG. 4B illustrates the actions performed by database 106 of node 102-2. For the purposes of illustration, the method shown in FIGS. 4A and 4B will be described with reference to FIGS. 1-3. The method shown in FIGS. 4A and 4B may be included in instructions contained in a memory of a robotic system or a memory associated with a node 102 and may be executed by one or more processors included in the robotic system or associated with a node 102.

As shown in FIGS. 4A and 4B, publishing node 102-1 having a server instance of a synchronization database 104 periodically transmits an advertise message (401), and a subscribing node 102, such as node 102-2 having a client instance of a synchronization database 106 executing thereon, periodically transmits a discover message (402). For example, database 104 and a client database 102 may respectively transmit an advertise message and a discover message upon an initial connection between publishing node 102-1 having database 104 and subscribing node 102 having database 106 or when database 104 and 106 start up. Consistent with some embodiments, the advertisement message may include information about attributes 108 that are stored in database 104. The discover message may indicate the attributes 108 that database 106 of subscribing node 102-2 requires. When database 104 of node 102-1 receives the discover message (403) from node 102-2, it will transmit a discover reply message (404) back to the subscribing node. When the subscribing node 102-2 receives an advertise message (405) from the publishing node or receives the discover reply message (406) from the publishing node, a server discovered callback (407) will be initiated by database 106 of subscribing node 102-2, informing the subscribing node that publishing node 102-1 having database 104 has been discovered. Subscribing node 102-2 will then transmit an add subscriber message to publishing node 102-1 (408). Consistent with some embodiments, the add subscriber message may indicate which attributes subscribing node 102-2 wants to subscribe to. When publishing node 102-1 receives the add subscriber message from subscribing node 102-2, database 104 of publishing node 102-1 will add the node 102-2 as a subscriber (409) and it to subscriber list 116. Adding subscribing node 102-2 as a subscriber will also initiate a subscriber added callback (410) that informs a publishing node 102-1 that a subscriber has been added. Once subscribing node 102-2 has been added to database 104 of publishing node 102-2 as a subscriber, database 104 will set flag 114 for all subscribed attributes (411) and wait for a sync-reply message from subscribing node 102-2 (412). While database 104 waits for the sync-reply message from subscribing node 102-2, modifications to attributes 108 are aggregated in database 104 until the sync-reply message is received. Thus, there is a built-in throttling of the information transmitted to database 106 of subscribing node 102-2, such that database 106 only receives an amount of information that it can accept.

Returning to FIGS. 4A and 4B, after subscribing node 102-2 transmits a sync-reply message (413), it will wait for a synchronization packet to be transmitted by publishing node 102-1 (414). Once publishing node 102-1 receives a sync-reply message from subscribing database 102-2, database 104 of publishing node 102-1 will determine if any attribute subscribed to subscribing node 102-2 has flag 114 set (415). If database 104 of publishing node 102-1 has just added client database 106 as a subscriber to one or more attributes, flag 114 for all attributes 108 will be set. Otherwise, flag 114 for attributes 108 will be set when an attribute 108 is modified, which database 104 will process when a modify-attribute call is received from the publishing application (416). If no attribute 108 has flag 114 set, database 104 will enter an idle state and wait for a publish call from the server application (417). If database 104 determines that there are still attributes 108 having flag 114 set and/or when database 104 receives a publish call (418), database 104 of publishing node 102-1 publishes one or more synchronization packets 200 that includes attributes 108 having flag 114 set (419), clears flag 114 for all published attributes 108 (420), and then proceeds to wait for a sync-reply signal from subscribing node 102-2 (412). When database 106 of subscribing node 102-2 receives the one or more synchronization packets 200 from publishing node 102-1 (421), database 106 updates attributes 108 stored therein (422) and checks to see, for every synchronization packet received, if the received packet is the final packet indicated as "end" in synchronization header 206 (423). If database 106 of subscribing node 102-2 determines that the received synchronization packet 200 is not the final packet, it will continue to wait for additional synchronization packets 200 from database 104 of publishing node 102-1 (414). If a received synchronization packet 200 is the final packet, database 106 of subscribing node 102-2 will initiate a client update callback (424), which will send a sync-reply message to publishing node 102-1 (413) and republish the updated attributes 108 to any downstream subscribers (425), such as nodes 102-3 to 102-N. Although not shown in FIGS. 4A and 4B, between steps 421 and 422, the client database may perform error detection on received synchronization packets 200. An example of an error detection method is described with respect to FIG. 5, below.

Figure 5:
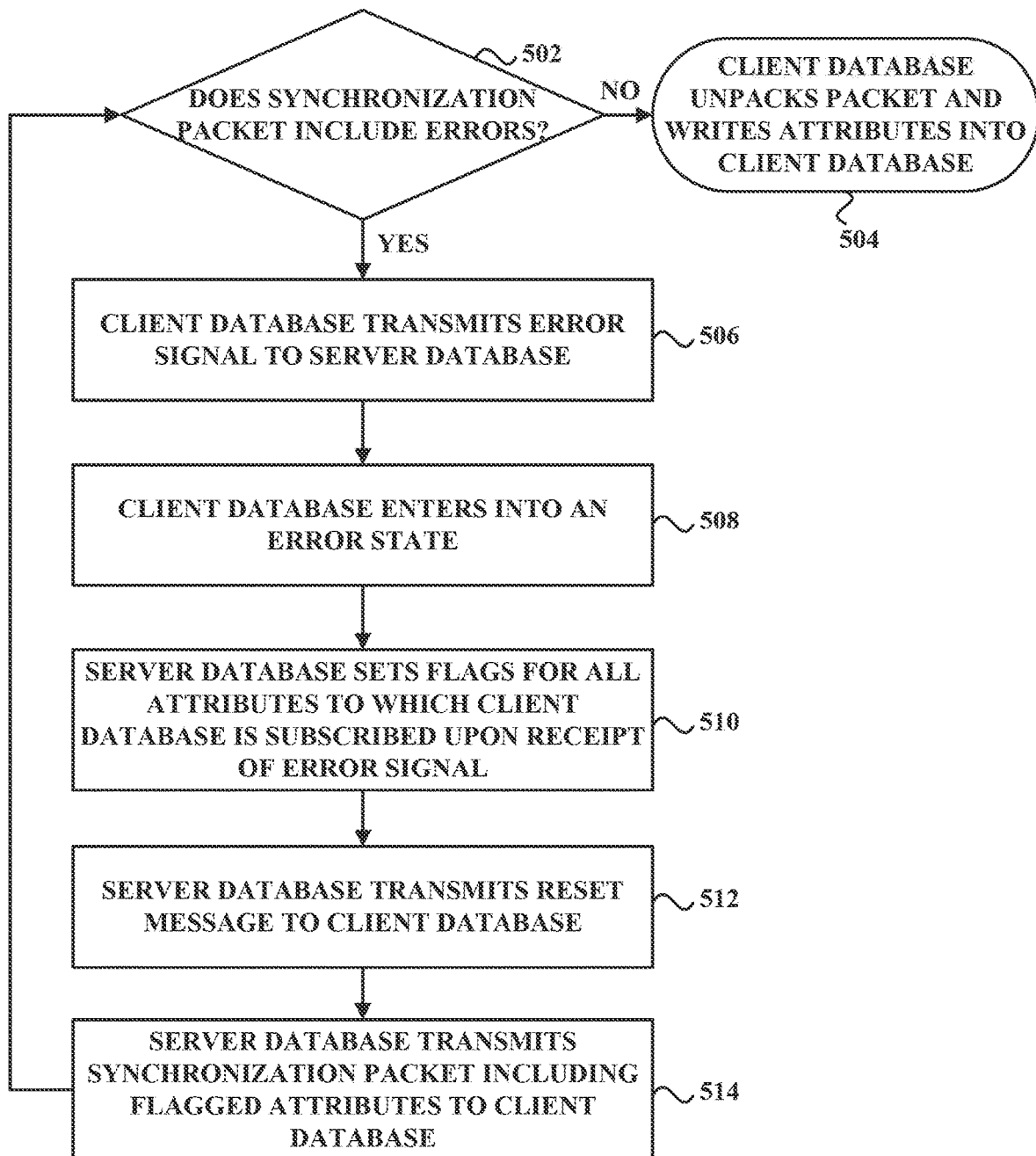
FIG. 5 is a flowchart illustrating an error detection method consistent with some embodiments.

FIG. 5 is a flowchart illustrating an error detection method consistent with some embodiments. For the purposes of illustration, the method shown in FIG. 5 will be described with reference to FIGS. 1-3. The method shown in FIG. 5 may be included in instructions contained in a memory of a robotic system or associated with a node 102 and may be executed by one or more processors included in the robotic system or associated with a node 102.

As shown in FIG. 5, after receiving a synchronization packet 200 from a publishing node such as node 102-1, a subscribing node, such as node 102-2, will scan synchronization packet 200 for errors (502). If no errors are found in synchronization packet 200, database 106 of subscribing node 102-2 will process synchronization packet 200 normally such that the attributes are unpacked and written into database 106 (504). If an error is detected, an error signal will be transmitted by subscribing node 102-2 to publishing node 102-1 (506). Subscribing node 102-2 will then enter into an error state wherein any further received synchronization packets 200 having a synchronization header 206 with a "start", "continue", or "end" indication will be discarded (508). Once publishing node 102-1 receives the error signal, database 104 will set flag 114 for all attributes to which subscribing node 102-2 is subscribed (510). Publishing node 102-1 then transmits a reset message, which may be a synchronization packet 200 having a synchronization header 206 with a "reset" indication, to subscribing node 102-2 (512). Consistent with some embodiments, the reset message may not include any payload and will serve to reset the expected sequence of attributes received by database 106 of subscribing node 102-2. Publishing node 102-1 then transmits synchronization packet 200 including flagged attributes to subscribing node 102-2 (514), and database 106 of subscribing node 102-2 will again scan synchronization packet 200 for errors (502). Consistent with some embodiments, if another error is found, another error signal will be sent and steps 506-514 will be performed again. Further consistent with some embodiments, database 104 of publishing node 102-1 may include a counter that counts the number of attempts to successfully transmit synchronization packet 200 to subscribing node 102-1 and will abort the transmission if the counter reaches a predetermined number. Database 104 may then log that an error has occurred and generate a timeout allowing database 104 to take any action for safety purposes or to correct the error on a timeout callback. The counter may be reset when publishing node 102-1 receives an acknowledgement message from subscribing node 102-2 indicating a successful transmission.

Embodiments as described in FIGS. 1-5 may be used in robotic systems to synchronize nodes of the robotic system with minimal system traffic and lag. Some embodiments may also be used in robot-assisted surgical systems to synchronize nodes of a robot-assisted surgical system in order to synchronize nodes with minimal system traffic and delay, making the system reliable and providing a near-real-time response to a surgeon's actions (e.g., a response in which the surgeon perceives no delay between commanding a system component to move or function and the actual motion or function). Examples of the use of system 100 are described in FIGS. 6-9, below.

Figure 6:
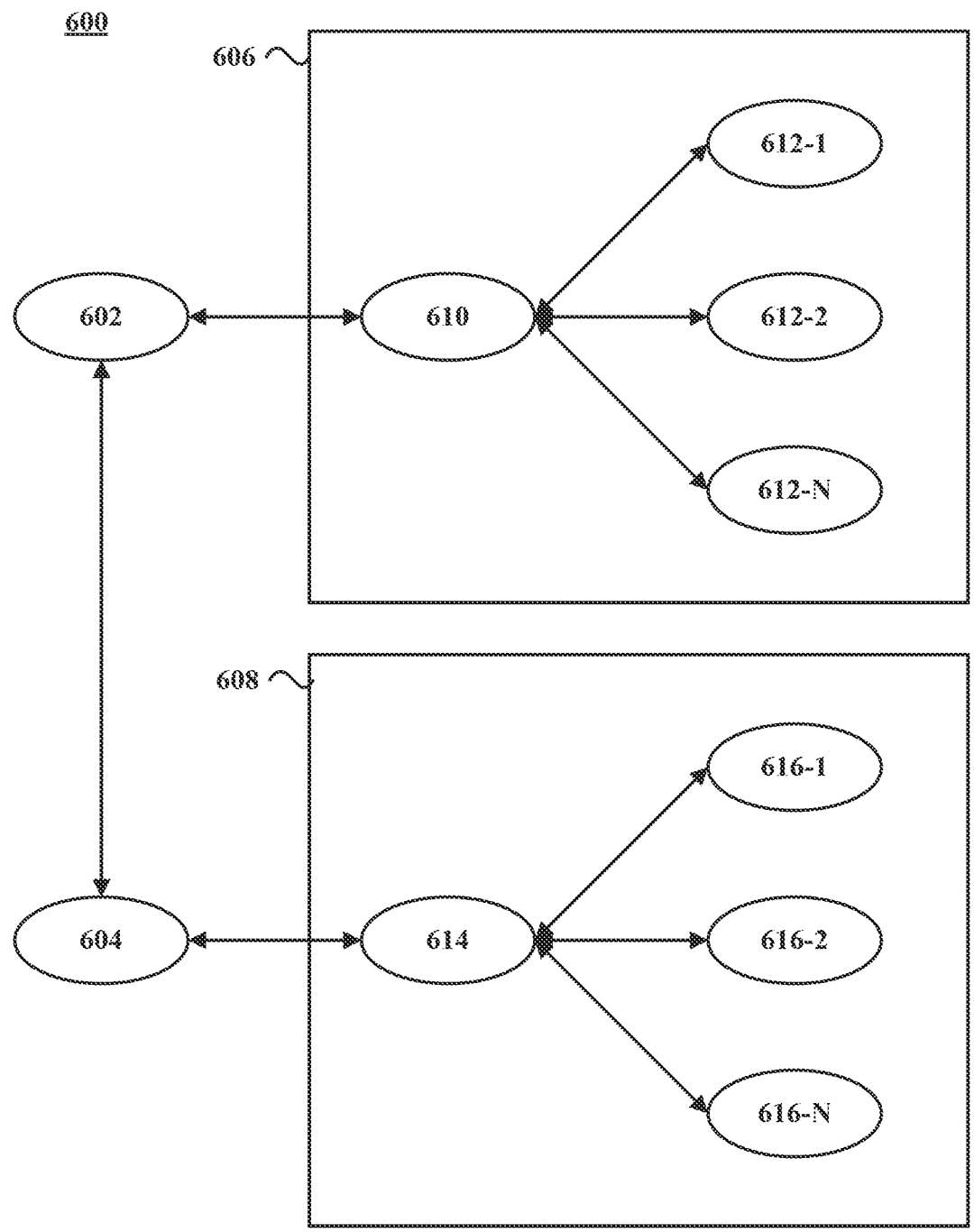
FIG. 6 is an example of the system of FIG. 1 being used in a robotic system, consistent with some embodiments.

FIG. 6 is an example of system 100 being used in a robotic system. As shown in FIG. 6, robotic system 600 includes a first unit controller 602 coupled to a second unit controller 604. Each of the unit controllers 602 and 604 are respectively coupled to a subsystem supervisor 606 and 608 as shown. Subsystem supervisor 606 includes a dispatcher 610 coupled to a plurality of mechanical manipulators 612-1 to 612-N. Subsystem supervisor 608 includes a dispatcher 614 coupled to a plurality of mechanical manipulators 616-1 to 616-N. Consistent with some embodiments, each unit controller, dispatcher, and manipulator may correspond to a node 102-1 to 102-N described above with respect to FIGS. 1 and 3. Moreover, each manipulator may correspond to a different mechanical part (e.g., a different link in a serial kinematic chain, a different actuator, a different sensor, a different system subgroup, etc.) of robotic system 600.

In accordance with some embodiments, dispatcher 610 acts as a subscribing node for each manipulator 612-1 to 612-N and for unit controller 602. That is, dispatcher 610 executes a client instance of a synchronization database for each manipulator 612-1 to 612-N and unit controller 602 so that dispatcher 610 subscribes to certain attributes available from unit controller 602 and subscribes to certain attributes available from each manipulator 612-1 to 612-N, all of which act as a publishing node to dispatcher 610. Dispatcher 610 may then republish attributes from unit controller 602 to manipulators 612-1 to 612-N and republish attributes from manipulators 612-1 to 612-N to unit controller 602. Using similar functionality, dispatcher 610 may act as a publisher/subscriber between other manipulators 612-1 to 612-N so that dispatcher 610 may synchronize attributes between manipulators 612-1 to 612-N. Furthermore, manipulators 612-1 to 612-N may be physically removed and added to system 600, or "hot-swapped", because when a new manipulator 612 is added, it will be capable of executing a client instance of a synchronization database to act as a subscribing node, and it will immediately subscribe to desired attributes, which will then be published to the added manipulator by dispatcher 610, thus providing the new manipulator with the latest states of the desired attributes. Dispatcher 614 provides similar functionality with respect to unit controller 604 and manipulators 616-1 to 616-N.

Figure 7:
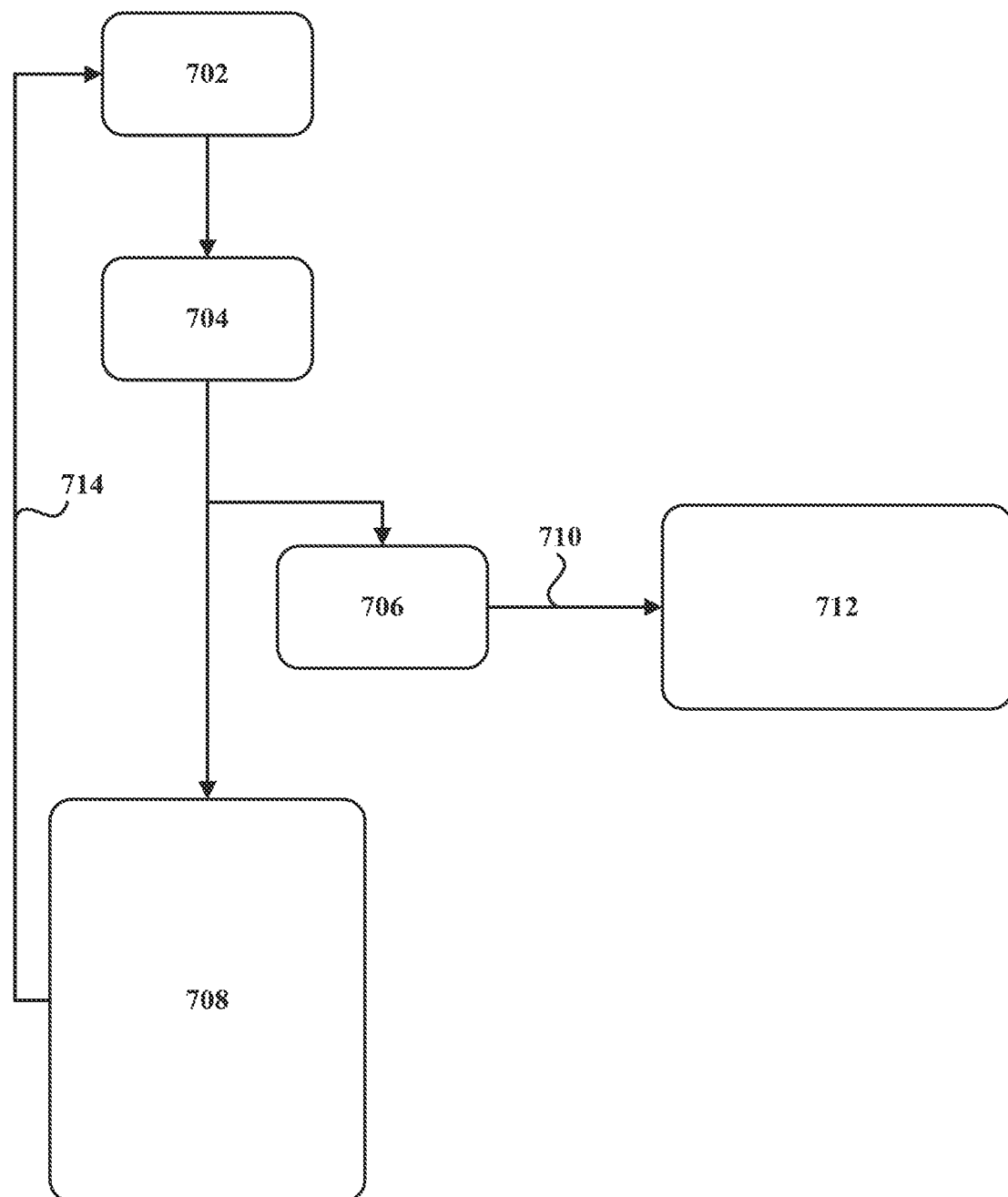
FIG. 7 is another example of the system of FIG. 1 being used in a robotic system, consistent with some embodiments.

FIG. 7 is another example of system 100 used in a robotic system, consistent with some embodiments. As shown in FIG. 7, system 700 includes a supervisor node 702 coupled to one or more synchronization databases 704. Consistent with some embodiments, supervisor node 702 transmits states of supervisor node 702 to one or more synchronization databases 704, which publish the received states to user interface (UI) node 706 and video subsystem node 708. In such an arrangement, supervisor node 702 executes a server instance of a synchronization database and acts as a publishing node, to which the one or more synchronization databases 704 execute a client instance of a synchronization database and acts as a subscribing node to supervisor node 702. One or more synchronization databases 704 then republish attributes and states of supervisor node 702 to UI node 706 and video subsystem node 708.

Consistent with some embodiments, UI node 706 may then interpret states of supervisor node 702 into actions 710 that are performed by one or more controllers 712 coupled to UI node 706. Similarly, video subsystem node 708 may interpret states of supervisor node 702 into commands for displaying video. As shown in FIG. 7, supervisor node 702 is also coupled to video subsystem node 708 to receive user interface events 714 from video subsystem node 708. Consistent with some embodiments, user interface events 714 may cause a change in a state of supervisor node 702, and the changed state will be flagged and then published to one or more synchronization databases 704 in accordance with embodiments described above. The use of synchronization databases to propagate a state in system 700 ensures UI node 706 and video subsystem node 708 will both update so as to be consistent with the state held by supervisor node 702. Video subsystem node 708 may additionally drive multiple displays, where the content for each display is determined by the state propagated via the synchronization database.

Figure 8:
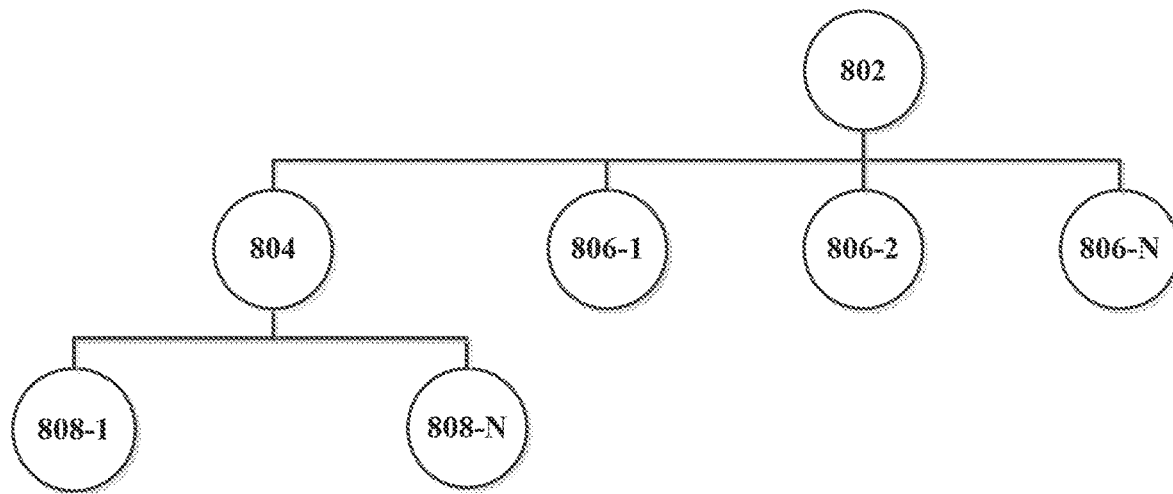
FIG. 8 is another example of the system of FIG. 1 being used in a robotic system, consistent with some embodiments.

FIG. 8 is an example of system 100 used in a robotic system 800, consistent with some embodiments. Robotic system 800 includes a plurality of nodes coupled together in a tree structure. Robotic system 800 includes a display controller node 802 that is coupled to a video pipeline node 804 and additional controller nodes 806. Video pipeline node 804 is coupled to further additional controller nodes 808-1 to 808-N. Consistent with some embodiments, robot system 800 synchronizes data across the nodes using a system similar to system 100. For example, video pipeline node 804 executes a client instance of a synchronization database and subscribes to further additional controller nodes 808-1-808-N, each of which are executing a server instance of a synchronization database and publishing attributes. Moreover, display controller node 802 executes a client instance of a synchronization database and subscribes to video pipeline node 804 and additional controller nodes 806-1 to 806-N, each of which are executing a server instance of a synchronization database and publishing attributes. Consequently, any attribute changes in further additional controller nodes 808 will be published to video processor node 804, and any attribute changes in video processor node 804 (including those received from further additional controller nodes 808) and additional controller nodes 806-1 to 806-N will be published to display controller node 802. Display controller node 802 in turn executes a "root" server database to re-publish one or more important "globally visible" states it has collected from subordinate nodes 804, 806-1 to 806-N (and 808-1 to 808-N, via 804). Subordinate nodes 804, and 806-1 to 806-N subscribe to this root database; node 808-1 to 808-N subscribes to node 804 for the root database content. Further, any newly added node to the tree structure will be able to execute a client instance of a synchronization database, subscribe to desired attributes, and be published the most recent state of the desired attributes, as described in previous embodiments.

Figure 9:
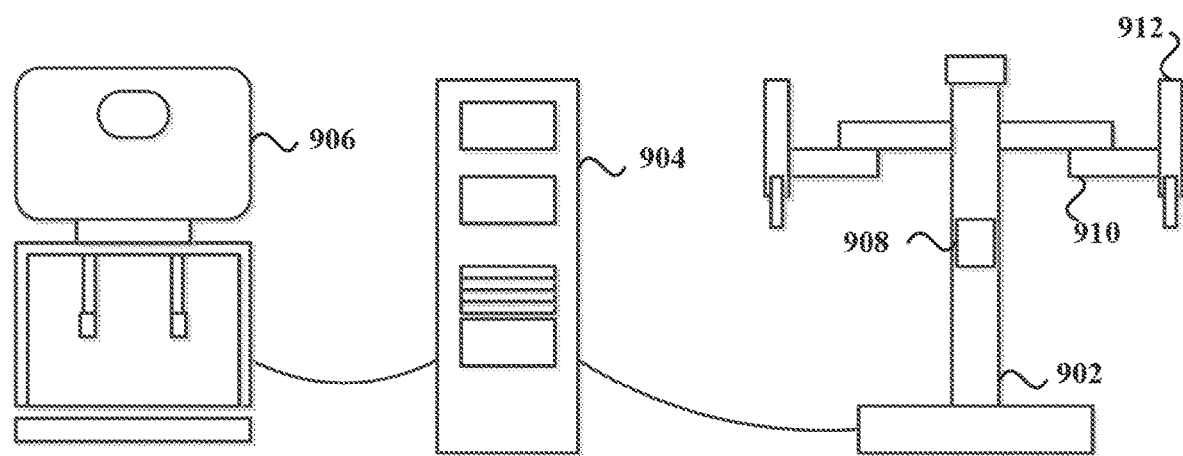
FIG. 9 is an example of the system of FIG. 1 being used in a robot-assisted surgical system, consistent with some embodiments.

FIG. 9 is an example of system 100 used in a robot-assisted surgical system 900, consistent with some embodiments. As shown in FIG. 9, system 900 includes a patient cart 902 coupled to a core system 904, which is in turn coupled to a surgeon console 906. Consistent with some embodiments, system 900 may correspond to a da Vinci® Surgical System commercialized by Intuitive Surgical, Inc. of Sunnyvale, California, such that patient cart 902 includes slave manipulator controlled surgical instruments (including a camera instrument), surgeon console 906 includes master controls for the slave manipulators, and core system 904 includes camera and vision system processing components in addition to other system data processing components. Further, each of patient cart 902, core system 904, and surgeon console 906 may be capable of executing one or more synchronization databases consistent with embodiments disclosed above, and may be referred to as nodes of system 900 Further, each of the nodes of system 900 may contain additional nodes. For example, patient cart 902 may include one or more processors that are each capable of executing a client instance of a synchronization database, and these one or more processors may be referred to as node 908 that subscribes to attributes published by individual nodes within patient cart 902, such as setup joint 910 and manipulator 912, each of which include associated processors that are executing a server instance of a synchronization database. Node 908, executing a client instance of a synchronization database, receives the published attributes from setup joint 910 and manipulator 912 and stores these attributes in the client instance of a synchronization database. These attributes may then be published by node 908 to core system 904, with node 908 executing a server instance of a synchronization database and core system 904 executing a client instance of a synchronization database. Similarly, node 908 may execute a client instance of a synchronization database for subscribing to attributes published from a server instance on core 904. A similar arrangement may be provided between core 904 and surgeon console 906 so that attributes may be synchronized across system 900.

Consistent with some embodiments, if patient cart 902 is disconnected from the rest of system 900, patient cart 902 can operate in a stand-alone environment in which node 908, executing a client instance of a synchronization database, receives the published attributes from robotic manipulator setup arm joint 910 and from manipulator clutch 912, and then stores these attributes in a client instance of a synchronization database. Upon reconnection with system 900, node 908 will publish its stored values to core 904, and then core 904 will publish its stored values to node 908 so that the data attributes throughout system 900 will be synchronized. The synchronization of system will operate similarly for the disconnection and subsequent reconnection of surgeon console 906 or any other system component for which an attribute database synchronization function is executed.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

Embodiments as disclosed herein may provide systems and methods for synchronizing nodes in a system with minimal system traffic and minimal collisions and interruption. Embodiments as disclosed herein may also provide systems and methods for synchronizing nodes in a system that allow a node to easily connect, disconnect, and reconnect to the system and be synchronized with minimal lag. Further, embodiments as disclosed herein may also provide systems and methods for synchronizing nodes in a system that allows a display at one node to me duplicated at another node with minimal lag. The examples provided above are exemplary only and are not intended to be limiting. One skilled in the art may readily devise other systems consistent with the disclosed embodiments which are intended to be within the scope of this disclosure. As such, the application is limited only by the following claims.

What is claimed is:

1. A synchronization system node comprising:
   one or more processors; and
   a synchronization database, the synchronization database comprising:
      a subscriber list of a plurality of subscribers,
      a first buffer including a plurality of attributes in a first state and
      a second buffer including the plurality of attributes in a second state,
   wherein the node is configured to:
   receive, from a publisher of the synchronization system, updates for one or more of the plurality of attributes;
   store, to the first buffer, the updates for the one or more of the plurality of attributes to update the plurality of attributes of the first buffer to an updated first state; and
   while receiving the updates from the publisher, publish, from the second buffer to a first subscriber of the plurality of subscribers, one or more of the plurality of attributes in the second state.

2. The synchronization system node of claim 1, wherein the node is further configured to:
   recognize when storing the updates to the first buffer is complete;
   responsive to the completion of the storing, transfer the plurality of attributes in the updated first state from the first buffer to the second buffer; and
   responsive to the completion of the storing, transfer the plurality of attributes in the second state from the second buffer to the first buffer.

3. The synchronization system node of claim 2, wherein the node is further configured to:
publish to the first subscriber of the plurality of subscribers one or more of the plurality of attributes in the updated first state from the second buffer.

4. The synchronization system node of claim 1, wherein receiving the updates for one or more of the plurality of attributes includes receiving a series of packets comprising the updates.

5. The synchronization system node of claim 4, wherein each packet of the series of packets includes a header comprising an indicator of the packet's order in the series of packets.

6. The synchronization system node of claim 5, wherein the node is further configured to recognize that the storing of the updates is complete if the indicator in the header is an end designation.

7. The synchronization system node of claim 1, wherein each attribute of the plurality of attributes includes data and a tag identifying the attribute.

8. The synchronization system node of claim 1, wherein the node is a component of a robot-assisted surgical system.

9. The synchronization system node of claim 8, wherein the node is a unit controller, a dispatcher, a manipulator, a supervisor, a video subsystem, or a user interface of the robot-assisted surgical system.

10. The synchronization system node of claim 8, wherein the node is a link in a kinematic chain, an actuator, a sensor, or a subgroup of the robot-assisted surgical system.

11. A method performed by a synchronization system node, the method comprising:
maintaining a subscriber list of a plurality of subscribers;
maintaining a first buffer including a plurality of attributes in a first state;
maintaining a second buffer including the plurality of attributes in a second state;
receiving updates for one or more of the plurality of attributes;
storing, to the first buffer of the node, the updates for the one or more of the plurality of attributes to update the plurality of attributes of the first buffer to an updated first state; and
while receiving the updates, publish, to a first subscriber of the plurality of subscribers, one or more of the plurality of attributes in the second state from the second buffer.

12. The method of claim 11, further comprising:
recognizing that storing the updates to the first buffer is complete;
responsive to the completion of the storing, transferring the plurality of attributes in the updated first state from the first buffer to the second buffer; and
responsive to the completion of the storing, transferring the plurality of attributes in the second state from the second buffer to the first buffer.

13. The method of claim 12, further comprising:
publishing to the first subscriber of the plurality of subscribers one or more of the plurality of attributes in the updated first state from the second buffer.

14. The method of claim 11, wherein receiving updates for one or more of the plurality of attributes includes receiving a series of packets comprising the updates.

15. The method of claim 14, wherein each packet of the series of packets includes a header comprising an indicator of the packet's order in the series of packets.

16. The method of claim 15, further comprising:
recognizing that the storing of the updates is complete when the indicator in the header is an end designation.

17. The method of claim 11, wherein each attribute of the plurality of attributes includes data and a tag identifying the attribute.

18. The method of claim 11, wherein the node is a component of a robot-assisted surgical system.

19. The method of claim 18, wherein the node is a unit controller, a dispatcher, a manipulator, a supervisor, a video subsystem, or a user interface of the robot-assisted surgical system.

20. The method of claim 18, wherein the node is a link in a kinematic chain, an actuator, a sensor, or a subgroup of the robot-assisted surgical system.

* * * * *